US009694301B2

(12) United States Patent
Choikhet et al.

(10) Patent No.: US 9,694,301 B2
(45) Date of Patent: Jul. 4, 2017

(54) TWO-DIMENSIONAL FLUID SEPARATION WITH CONTROLLED PRESSURE

(75) Inventors: Konstantin Choikhet, Karlsruhe (DE); Klaus Witt, Keltern (DE)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 14/400,312

(22) PCT Filed: May 10, 2012

(86) PCT No.: PCT/EP2012/058695
§ 371 (c)(1),
(2), (4) Date: Nov. 10, 2014

(87) PCT Pub. No.: WO2013/167193
PCT Pub. Date: Nov. 14, 2013

(65) Prior Publication Data
US 2015/0122655 A1   May 7, 2015

(51) Int. Cl.
*B01D 15/18* (2006.01)
*G01N 30/32* (2006.01)
(Continued)

(52) U.S. Cl.
CPC ....... *B01D 15/18* (2013.01); *G01N 27/44704* (2013.01); *G01N 30/32* (2013.01);
(Continued)

(58) Field of Classification Search
CPC ........ G01N 30/20; G01N 30/32; G01N 30/46; G01N 2030/201; G01N 2030/202; G01N 2030/328
See application file for complete search history.

(56) References Cited

U.S. PATENT DOCUMENTS 3,925,019 A * 12/1975 Hamish .................... B01J 39/26
                                                    210/284
3,926,559 A * 12/1975 Stevens ................ G01N 30/461
                                                    210/284
(Continued)

FOREIGN PATENT DOCUMENTS

WO   WO2009062538 A1   5/2009
WO   WO2012175111 A1   12/2012

OTHER PUBLICATIONS

Tranchida et al. "A flexible loop-type flow modulator for comprehensive two-dimensional gas chromatography", Journal of Chromatography A, vol. 1218, No. 21, May 2011.
(Continued)

*Primary Examiner* — Brian R Gordon

(57) ABSTRACT

A sample separation apparatus for separating a liquid sample includes a first separation unit for separating the sample, a first fluid drive for conducting the sample to be separated through the first separation unit, a second separation unit, arranged downstream of the first separation unit, for further separating the sample, a second fluid drive for at least partially conducting the sample through the second separation unit, and a fluidic valve having interfaces fluidically coupled to the first and second fluid drives and being switchable for performing the separation of the sample. The apparatus is configured for adjusting a pressure at a predefined position to a predefined value, wherein the predefined position is in a fluidic path between an outlet of the first separation unit and an inlet of the second separation unit or in fluid communication with this fluidic path.

38 Claims, 2 Drawing Sheets

(51) Int. Cl.
  *G01N 30/46*   (2006.01)
  *G01N 27/447*  (2006.01)
  *G01N 30/72*   (2006.01)
  *G01N 30/34*       (2006.01)
  *G01N 30/60*       (2006.01)

(52) U.S. Cl.
  CPC ......... *G01N 30/463* (2013.01); *G01N 30/465* (2013.01); *G01N 30/72* (2013.01); *G01N 30/34* (2013.01); *G01N 30/6095* (2013.01); *G01N 2030/322* (2013.01); *G01N 2030/328* (2013.01)

(56) References Cited

U.S. PATENT DOCUMENTS

| | | | | |
|---|---|---|---|---|
| 4,274,967 | A * | 6/1981 | Snyder | G01N 30/461 |
| | | | | 210/198.2 |
| 4,567,753 | A * | 2/1986 | Miller, Jr. | G01N 30/96 |
| | | | | 356/72 |
| 4,851,355 | A * | 7/1989 | Hayes, Jr. | G01N 30/40 |
| | | | | 422/70 |
| 5,468,643 | A * | 11/1995 | Su | G01N 30/16 |
| | | | | 210/198.2 |
| 5,538,689 | A * | 7/1996 | Dybdahl | G01N 33/1813 |
| | | | | 210/638 |
| 6,093,327 | A * | 7/2000 | Anderson, Jr. | B01D 15/3885 |
| | | | | 210/198.2 |
| 6,296,771 | B1 * | 10/2001 | Miroslav | G01N 30/466 |
| | | | | 210/143 |
| 7,767,463 | B2 * | 8/2010 | Quinn | G01N 30/34 |
| | | | | 436/161 |
| 2002/0150926 | A1 * | 10/2002 | Jindal | G01N 30/463 |
| | | | | 435/6.12 |
| 2006/0186028 | A1 * | 8/2006 | Hughes | G01N 30/10 |
| | | | | 210/198.2 |
| 2006/0219638 | A1 * | 10/2006 | Watanabe | G01N 30/463 |
| | | | | 210/656 |
| 2007/0074766 | A1 | 4/2007 | Klee et al. | |
| 2010/0101411 | A1 | 4/2010 | Tipler | |

OTHER PUBLICATIONS

Filgueira, et al. "Improving peak capacity in fast online comprehensive two-dimensional liquid chromatography with post-first-dimension flow splitting", Analytical Chemistry, vol. 83, No. 24, Dec. 15, 2011.

Bedani, et al. "A theoretical basis for parameter selection and instrument design in comprehensive size-exclusion chromatography x liquid chromatography", Journal of Chromatography, vol. 1133, No. 1-2, Nov. 10, 2006.

Verstraeten, et al. "Comparison of quantitative performance of constant pressure versus constant flow rate gradient elution separations using concentration-sensitive detectors", Journal of Chromatography, vol. 1232, Oct. 12, 2011.

International Search Report and Written Opinion mailed Jan. 17, 2013 in International Application No. PCT/EP2012/058695.

Chinese Office action dated Dec. 3, 2015 from related Chinese Patent Application No. 201280073067.7.

* cited by examiner

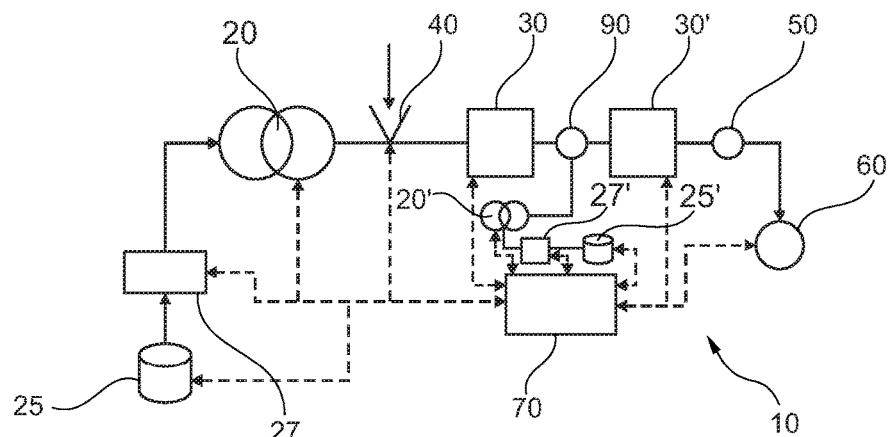
Fig. 1
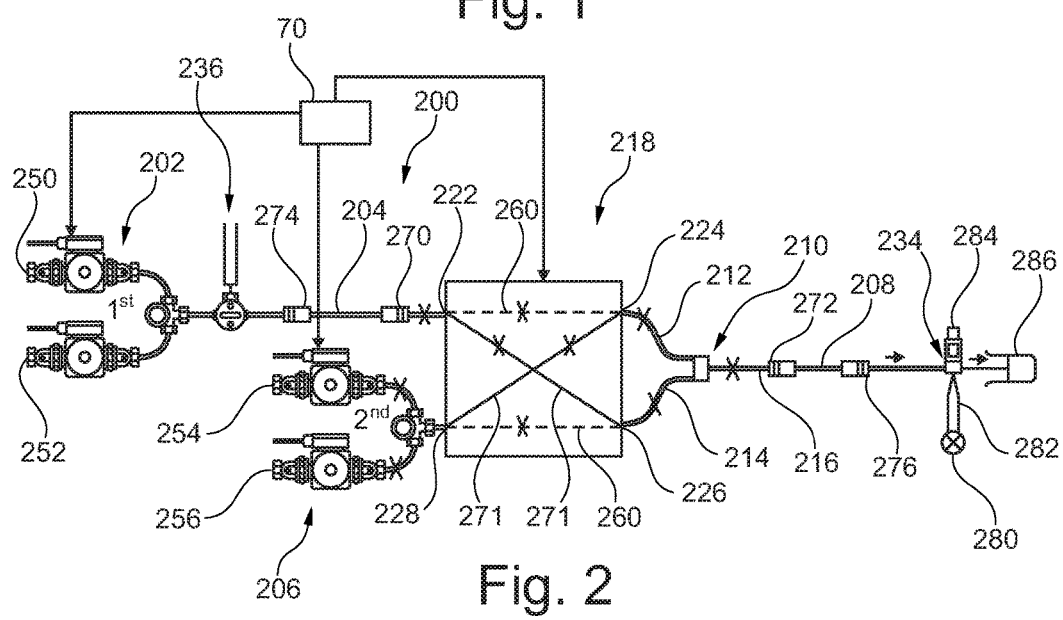
Fig. 2
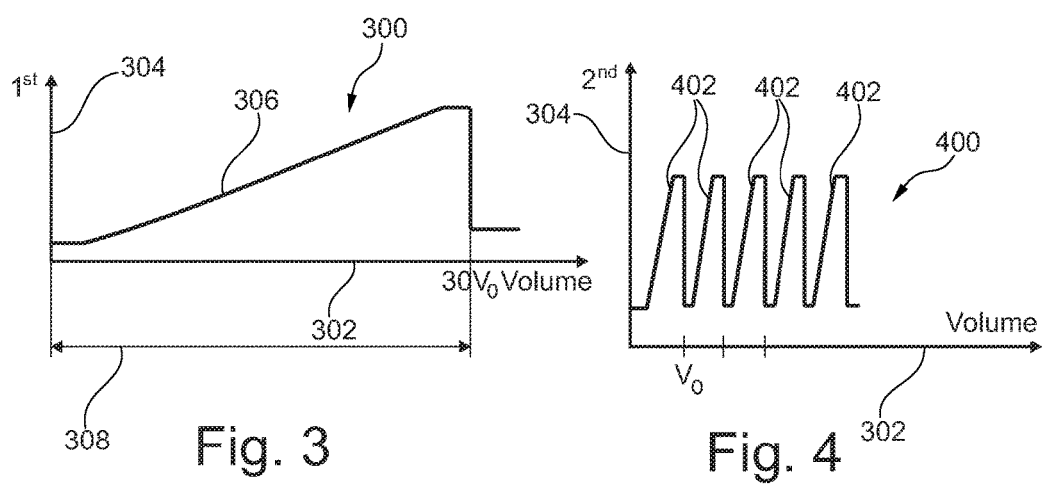
Fig. 3
Fig. 4

# TWO-DIMENSIONAL FLUID SEPARATION WITH CONTROLLED PRESSURE

The present application is a National Stage Application under 35 U.S.C. §371 and claims priority under 35 U.S.C. §121 from International Patent Application No. PCT/EP2012/058695 filed on May 10, 2012. The entire disclosure of International Patent Application No. PCT/EP2012/058695 is specifically incorporated herein by reference.

BACKGROUND ART

The present invention relates to a sample separation system.

In liquid chromatography, a fluidic sample and an eluent (liquid mobile phase) may be pumped through conduits and a column in which separation of sample components takes place. The column may comprise a material which is capable of separating different components of the fluidic analyte. Such a packing material, so-called beads which may comprise silica gel, may be filled into a column tube which may be connected to other elements (like a sampler, a detector) by conduits.

The composition of the mobile phase can be adjusted by composing the mobile phase from different fluidic components with variable contributions, so called gradient mode. HPLC systems often are operated in such a gradient mode, wherein for instance for reversed phase chromatography the organic content is ramped over time, or for ion exchange chromatography the salt content is ramped over time. Especially in peptide or protein analysis most applications are based on water/acetonitrile gradients. An analytical protocol for running a defined analytical process is called the "method". In the analytical protocol—or method—for a gradient separation, the gradient is usually defined as a composition change program over time, while the flow rate is kept constant. The so-called retention time is a time required for transport of a certain component of a fluidic sample to be separated throughout a separation column during a gradient run.

Alternatives to the concept of retention times are known such as the concept of retention volumes. Particularly, WO 2009/062538 A1 discloses in a high performance liquid chromatography system, wherein a mobile phase is driven through a stationary phase for separating components of a fluidic sample comprised in the mobile phase, a flow rate of the mobile phase may not be constant and may depend on a variation in a control value in the system. WO 2009/062538 A1 comprises determining (for instance by an adequate analysis unit, which considers predicted, measured or elsewise derived flow information) a value of a retention volume representing such volume of the mobile phase required to elute a respective compound of the fluidic sample at least through the separating device. The mobile phase drive is then operated (for instance by an adequate control unit) based on the determined value of the volume delivered into the system. This makes use of the concept of retention volumes, rather than retention times.

Two-dimensional separation of a fluidic sample denotes a separation technique in which a first separation procedure in a first separation unit is performed to separate a fluidic sample into a plurality of fractions, and in which a subsequent second separation procedure in a second separation unit is performed to further separate at least one of the plurality of fractions into sub-fractions. Two-dimensional liquid chromatography (2D LC) may combine two liquid chromatography separation techniques and plot the time dependency of detection events along two orthogonal time axes.

DISCLOSURE

It is an object of the invention to provide an efficiently operating sample separation apparatus.

According to an exemplary embodiment of the present invention, a sample separation apparatus for separating a fluidic sample is provided, the sample separation apparatus comprising a first separation unit for separating the fluidic sample, a first fluid drive configured for conducting the fluidic sample to be separated through the first separation unit, a second separation unit, arranged downstream of the first separation unit, for further separating at least part of the fluidic sample (for instance a fraction of it or its constituents, or at least parts thereof) after treatment by the first separation unit, a second fluid drive configured for at least partially conducting the fluidic sample, after treatment by the first separation unit, through the second separation unit, and a fluidic valve having fluidic interfaces fluidically coupled to the first fluid drive, particularly fluidically coupled to the first fluid drive via the first separation unit, and fluidically coupled to the second fluid drive and being switchable for performing the separation of the fluidic sample, wherein the sample separation apparatus is configured for adjusting a pressure at a predefined position to a predefined value, wherein the predefined position is in a fluidic path between an outlet of the first separation unit and an inlet of the second separation unit or in (particularly direct, i.e. without a fluidic impedance in between) fluid communication with this fluidic path. The two separation units may be in direct fluid connection to one another (so that fluidic sample may first be pumped through the first separation unit before at least part of the same fluidic sample is pumped through the second separation unit.

According to another exemplary embodiment of the present invention, a method of separating a fluidic sample is provided, wherein the method comprises conducting the fluidic sample to be separated through a first separation unit by a first fluid drive, conducting the fluidic sample after treatment by the first separation unit through a second separation unit downstream of the first separation unit, switching a fluidic valve having fluidic interfaces fluidically coupled to the first fluid drive and a second fluid drive (influencing at least a part of the fluidic sample before supply to the second separation unit) for performing the separation of the fluidic sample, and adjusting a pressure at a predefined position to a predefined value, wherein the predefined position is located in a fluidic path between an outlet of the first separation unit and an inlet of the second separation unit or in fluid communication with this fluidic path.

According to still another exemplary embodiment of the present invention, a software program or product is provided, preferably stored on a data carrier, for controlling or executing the method having the above mentioned features, when run on a data processing system such as a computer.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in the context of fluid separation control. The fluid separation control scheme according to an embodiment of the invention can be performed or assisted by a computer program, i.e. by software, or by using one or more special electronic optimization circuits, i.e. in hardware, or in hybrid form, i.e. by means of software components and hardware components.

In the context of this application, the term "fluidic sample" may particularly denote any liquid and/or gaseous medium, optionally including also solid particles, which is to be analyzed. Such a fluidic sample may comprise a plurality of fractions of molecules or particles which shall be separated, for instance biomolecules such as proteins. Since separation of a fluidic sample into fractions involves a certain separation criterion (such as mass, volume, chemical properties, etc.) according to which a separation is carried out, each separated fraction may be further separated by another separation criterion (such as mass, volume, chemical properties, etc.) or finer separated by the first separation criterion, thereby splitting up or separating a separate fraction into a plurality of sub-fractions.

In the context of this application, the term "fraction" may particularly denote such a group of molecules or particles of a fluidic sample which have a certain property (such as mass, charge, volume, chemical properties or interaction, etc.) in common according to which the separation has been carried out. However, molecules or particles relating to one fraction can still have some degree of heterogeneity, i.e. can be further separated in accordance with another separation criterion. As well the term "fraction" may denote a portion of a solvent containing the aforementioned group of molecules.

In the context of this application, the term "sub-fractions" may particularly denote individual groups of molecules or particles all relating to a certain fraction which still differ from one another regarding a certain property (such as mass, volume, chemical properties, etc.). Hence, applying another separation criterion for the second separation as compared to the separation criterion for the first separation allows these groups to be further separated from one another by applying the other separation criterion, thereby obtaining the further separated sub-fractions. As well the term "sub-fraction" may denote a portion of a solvent containing the aforementioned individual group of molecules.

In the context of this application, the term "downstream" may particularly denote that a fluidic member located downstream compared to another fluidic member will only be brought in interaction with a fluidic sample after interaction with the other fluidic member (hence being arranged upstream). Therefore, the terms "downstream" and "upstream" relate to a flowing direction of the fluidic sample. The terms "downstream" and "upstream" may also relate to a preferred direction of the fluid flow between the two members being in downstream-upstream relation.

In the context of this application, the term "sample separation apparatus" may particularly denote any apparatus which is capable of separating different fractions of a fluidic sample by applying a certain separation technique. Particularly, two separation units may be provided in such a sample separation apparatus when being configured for a two-dimensional separation. This means that the sample is first separated in accordance with a first separation criterion, and at least one or some of the fractions resulting from the first separation are subsequently separated in accordance with a second, different, separation criterion or more finely separated in accordance with the first separation criterion.

The term "separation unit" may particularly denote a fluidic member through which a fluidic sample is transferred and which is configured so that, upon conducting the fluidic sample through the separation unit, the fluidic sample will be separated into different groups of molecules or particles (called fractions or sub-fractions, respectively). An example for a separation unit is a liquid chromatography column which is capable of trapping or retarding and selectively releasing different fractions of the fluidic sample.

In the context of this application, the term "fluid drive" may particularly denote any kind of pump which is configured for conducting a mobile phase and/or a fluidic sample along a fluidic path. A corresponding liquid supply system may be configured for delivery of a single liquid or of two or more liquids in controlled proportions and for supplying a resultant mixture as a mobile phase. It is possible to provide a plurality of solvent supply lines, each fluidically connected with a respective reservoir containing a respective liquid, a proportioning valve interposed between the solvent supply lines and the inlet of the fluid drive, the proportioning valve configured for modulating solvent composition by sequentially coupling selected ones of the solvent supply lines with the inlet of the fluid drive, wherein the fluid drive is configured for taking in liquids from the selected solvent supply lines and for supplying a mixture of the liquids at its outlet. More particularly, the first fluid drive can be configured to conduct the fluidic sample, usually mixed with, or injected into a flow of a mobile phase (solvent composition), through the first separation unit, whereas the second fluid drive can be configured for conducting the fluidic sample fractions, usually mixed with a further mobile phase (solvent composition), after treatment by the first separation unit through the second separation unit.

In the context of this application, the term "flow coupler" may particularly denote a fluidic component which is capable of unifying flow components from two fluid inlet terminals into one common fluid outlet terminal. For example, a bifurcated flow path may be provided in which two streams of fluids flow towards a bifurcation point are unified to flow together through the fluid outlet terminal. At a bifurcation point where the fluid inlet terminals and the fluid outlet terminal are fluidically connected, fluid may flow from any source terminal to any destination terminal depending on actual pressure conditions, thereby allowing for some sort of equilibration. The flow coupler may act as a flow combiner for combining flow streams from the two fluid inlet terminals further flowing to the fluid outlet terminal. The flow coupler may provide for a permanent (or for a selective) fluid communication between the respective fluid terminals and connected conduits, thereby allowing for a pressure equilibration between these conduits. In certain embodiments, the flow coupler may also act as a flow splitter.

In the context of this application, the term "fluidic valve" may particularly denote a fluidic component which has fluidic interfaces, wherein upon switching the fluidic valve selective ones of the fluidic interfaces may be selectively coupled to one another so as to allow fluid to flow along a corresponding fluidic path, or may be decoupled from one another, thereby disabling fluid communication.

In the context of this application, the terms "fluid inlet terminals" and "fluid outlet terminal" may particularly indicate that in a general flowing direction of fluid through the device, the fluid will be conducted via at least one of the fluid inlet terminals towards the flow coupler and from there towards the fluid outlet terminal. However, this terminology does not exclude (at least temporarily) other flow directions, for instance a fluid flow from one of the fluid inlet terminals into the other one via the flow combiner, for instance for pressure equilibration purpose. In a similar way, this terminology does also not exclude that, in a certain operation mode, there may also be temporarily a backflow from the fluid outlet terminal to at least one of the fluid inlet terminals.

According to an exemplary embodiment of the invention, a two-dimensional sample separation system is provided which operates with a controlled (particularly constant or essentially constant over time) pressure in a fluidic system segment, between two separation units. Particularly, by maintaining the pressure constant at at least one position in such a segment, preferably over the entire segment, it is possible to operate one or both of the separation units at a predefined pressure value. It should be kept in mind that, due to steep gradients which may be employed in comprehensive 2D-LC, there may be a very frequent and rapid change in viscosity, which is a systematic and otherwise unavoidable pressure dynamics which can be suppressed or even eliminated by embodiments of the invention. Thus, the mechanical stress acting on the separation units can be predicted, is reproducible and may even be kept constant so that the lifetime over which the separation unit(s) may be maintained within the sample separation system without maintenance or change may be significantly increased. Embodiments of the invention are based on the consideration that in contrast to conventional approaches it is not a strict requirement to keep the flow rate through the fluid supply units and the separation units constant over the sample separation procedure. In contrast to this, exemplary embodiments of the invention allow to vary this flow rate, but to consider the pressure along the sample separation path as the controllable parameter which can be set to a predefined or even constant value. A corresponding sample separation control scheme is applied by embodiments of the present invention to a two-dimensional sample separation architecture in which the fluidic sample is firstly separated into fractions by applying a first separation criterion, and subsequently each separated fraction may be further separated into sub-fractions by applying a different second separation criterion.

In the following, further exemplary embodiments of the sample separation system will be explained. However, these embodiments also apply to the method, and the software program or product.

In an embodiment, the sample separation apparatus is configured for adjusting the pressure at the position to a constant value, i.e. to a target pressure value which is maintained constant over time. Therefore, a control device or the like may control the pressure at the position, more preferably in the entire fluidic path between the two separation units (optionally also including the separation units themselves) towards a constant value which does not change over time. The $1^{st}$-D column will see a stable pressure level at its end. So the $1^{st}$-D separation is undisturbed. But also the internal pressure forces, although at a high level, will stay constant (less dynamic). The $2^{nd}$-D column will see a stable pressure at its inlet, so the internal pressure forces, although gradually reducing to its end, will stay constant (less dynamic). By preventing sudden pressure pulses or pressure shock on fluidic components such as the separation column(s) it is possible to decrease deterioration or damage of the fluidic components at a corresponding position or in a corresponding segment of a fluidic system.

In an embodiment, the second fluid drive is controllable for adjusting the pressure at the position to the predefined (particularly constant) value. In this embodiment, the control of the second fluid supply unit, i.e. the pump providing the fluid flow to the second separation unit only, may be configured so that the criterion of maintaining the predefined pressure at least at the position or over a segment is fulfilled.

It has turned out to be simple and efficient to control the commanded flow value of the second pump for a precise pressure adjustment. Alternatively the drive torque can be adjusted, resulting in a corresponding pressure level.

In an embodiment, the second fluid drive is controllable for adjusting the pressure at the position to follow a predefined course. Such a predefined course may be any desired function, relation or other course defined by a parameter set and defines a trace over time that the pressure is required to precisely follow. The pressure may be adjusted at the predefined position by controlling the flow rate of the second fluid drive.

In an embodiment, the second fluid drive is controllable for adjusting a flow rate at the position to a previously calibrated value. Thus, not only the pressure may be a controlled parameter, it is also possible that the flow rate is set to a defined value or to follow a predefined time-dependency resulting in that the pressure follows a predicted or projected trajectory, particularly in that the pressure remains constant.

In an embodiment, at least one of the first fluid drive and the second fluid drive is controllable for adjusting a ratio between a flow rate at the position and a flow rate generated by the first fluid drive to a predefined value, particularly to a constant value, more particularly to follow a predefined course, whereas the first fluid drive is the drive providing the flow to the first (upstream) separation unit. This may then allow to keep the dilution of the mobile phase at the fluid junction reproducible (particularly constant) even in case of a variation of the restriction values of the parts or components of the fluidic system.

In an embodiment, the pressure may be adjusted at the predefined position even when a composition of the mobile phase is commanded by a gradient program of the second fluid drive, which will change the viscosity of the fluid flowing through the second separation unit. Thus, the control logic may predict and/or consider such an effect and may compensate for it. Prediction may be supported by stored information about solvent properties and the resulting viscosity based on composition of the mobile phase. Alternatively the prediction may result from recording the observed values in a scouting run.

In an embodiment, a flow rate through the second fluid drive is controllable for adjusting the pressure at the position to the predefined value. The flow rate may be the fluid volume conveyed by the second fluid drive per time interval. In this embodiment, the modified parameter is the flow rate and the parameter which is adjusted towards a target value as a result of the adjustment of the flow rate is the pressure.

In an embodiment, the sample separation apparatus is configured for regulating the pressure at the position to the predefined value based on a sensor value indicative of an actual pressure value at the position. For this purpose, at least one pressure sensor or pressure determination unit may be located at the position in the fluidic path between the sample separation units in a fluidic connection to such a position for sensing the actual pressure value. Therefore, a feedback control loop may be implemented to measure the pressure value either at the desired position or at a position in fluid communication with this position so as to derive the actual value of the pressure at this position. Hence, in case the sensor value indicates that the actual or real pressure deviates from a predefined target value, the sample separation apparatus or components thereof (particularly the second fluid supply unit) can be controlled differently so as to cause an adjustment of the pressure at the position from the actual value to the actual target value. Such a sensor may be a pressure sensor, a flow sensor, a temperature sensor, a density sensor, a deflection sensor or any other kind of sensor capable of deriving pressure information.

In an embodiment, the sample separation apparatus is configured for adjusting the pressure at the position being located downstream of the fluidic valve to the predefined value. Hence, in this embodiment, the pressure-controlled position is located downstream of the fluidic valve which, in turn, is positioned upstream of the second separating unit. Therefore, it can be ensured in the separating unit that the inlet pressure is maintained at a constant or at least defined value, thereby protecting particularly the second separating unit from deterioration due to strong and periodic/frequent changes of the pressure over time. However, it is also possible that the position is located upstream of the fluidic valve as long as it is located downstream of the first separation unit.

In an alternative embodiment, the sample separation apparatus is configured for adjusting the pressure at the position located at an outlet or downstream of the second fluid drive to the predefined value. For instance, a pressure sensor may be located at this outlet position, and operation of the second fluid drive (and/or of the first fluid drive and/or the fluidic valve and/or of any other fluidic component) may be modified to maintain the pressure at the measurement position at a constant or time-dependent target value.

In an embodiment, the sample separation apparatus is configured for adjusting the pressure to the predefined value in an entire segment between the first separation unit and the second separation unit. Thus, not only a certain position may be kept at the predefined, particularly constant, pressure value as a result of a corresponding control of at least one fluid supply unit and/or the fluidic valve, but particularly the full fluidic path between outlet of the first separation unit and inlet of the second separation unit may be operated under these well-defined conditions. Hence, all fluidic members located along this fluidic path or connected to it may be prevented from deterioration caused by severe variations or insufficient control over pressure conditions.

In an embodiment, the sample separation apparatus is configured for separating the fluidic sample in accordance with a volume-based control scheme which is executed by controlling run volumes of fluid flowing over at least one of the separation units, whereas evaluation of the sample separation is performed in terms of retention volumes required for releasing fractions of the fluidic sample from at least one of the separation units. Hence, operation may be based on a control of retention volumes (rather than of retention times), in one of or particularly in both dimensions of the sample separation scheme. This may include determining (for instance by an adequate analysis unit, which considers predicted, measured or elsewise derived flow information) a value of a respective delivered volume representing such volume of the mobile phase that has been delivered into or through a separation unit since a separation begin, run begin or any other reference point in course of analysis. In such a preferred embodiment, the two-dimensional sample separation apparatus is operated in accordance with a volume based control scheme. Unlike conventional approaches, such an embodiment does not require the flow rate to be necessarily kept constant and does not rely on the retention time as an axis of a separation progress, but in contrast to this records or registers release of fractions and subfractions of a fluidic sample from a separation column in terms of a volume of a mobile phase needed to release the fraction of the fluidic sample from the respective separating unit. Applying a volume-based operation mode makes it possible to operate the system with a constant pressure at one or both of the separation units, thereby protecting those from mechanical stress caused by strong pressure variations.

In an embodiment, the sample separation apparatus is configured for separating the fluidic sample by modifying a flow rate through at least one of the first fluid drive and the second fluid drive. By taking this approach, the pressure may be kept constant at a position or even over at least a sub-segment of the fluidic path between outlet of the first separating unit and inlet of the second separating unit, which protects one or more fluidic devices located along this path.

When the sample separation system is a liquid chromatography system such as a HPLC, the first separation unit and/or the second separation unit may be a liquid chromatography column.

In an embodiment, the first separation unit is arranged between (particularly downstream of) the first fluid drive and (particularly upstream of) the corresponding fluidic interface of the fluidic valve. Therefore, the first fluid drive may be fluidically coupled to its assigned fluidic interface of the fluidic valve indirectly via the first fluid separation unit. Hence, the first fluid drive may be operative to conduct the fluidic sample through the first separation unit. Before the separation by the first separation unit, the first fluid drive may add a mobile phase (i.e. a solvent composition which may be varied over time by the first fluid drive and an assigned proportioning valve) to the fluidic sample. For example, it is possible that the first fluid drive varies a solvent composition over time so as to carry out a gradient run in the first separation unit. Thereby, the fluidic sample may be separated into multiple fluidic components or fractions at an outlet of the first separation unit by liquid chromatography. In an alternative embodiment, at least one of the first separation and the second separations relates to an isocratic chromatographic run.

In an embodiment, the second separation unit for further separating the fluidic sample after treatment (usually separation) by the first separation unit may be arranged downstream of the first separation unit and downstream of the fluidic valve so as to further separate the already separated fractions of the fluidic sample into sub-fractions. For this purpose, it may be advantageous that the second separation unit operates in accordance with another separation criterion or even separation technique as compared to the first separation unit.

In an embodiment, the sample separation apparatus comprises a flow coupler having two fluid inlet terminals and a fluid outlet terminal in fluid communication with one another, the fluid outlet terminal being fluidically connectable to the second separation unit directly or via further arrangements, such as flow reactors, delay lines or others.

In an embodiment, the second separation unit is arranged at the fluid outlet terminal of a flow coupler. Therefore, the fluidic sample separated or treated by the first separating unit (including solvent or mobile phase provided by the first fluid drive) as well as a solvent provided by the second fluid drive may be mixed at the junction point of the flow coupler and may together be coupled into the second separation unit.

In an embodiment, the flow coupler is configured as a fluidic T-piece, a fluidic Y-piece, or a fluidic X-piece, In case of a fluidic T piece and a fluidic Y piece, two flow streams are combined at one bifurcation point into a single outlet path. In the case of a fluidic X piece, there may be one further fluid conduit. This further fluid conduit can be a second fluid outlet conduit or a third fluid inlet conduit. Other kinds of flow couplers are possible as well.

In an embodiment, the flow coupler may comprise at least one check valve preventing fluid from flowing in a reversed direction in at least one of the terminals. This may eliminate undesired back flow of fluid in an unwanted direction.

In an embodiment, the fluidic valve comprises a first valve member and a second valve member being movable, particularly being rotatable, relative to one another to thereby adjust different operation modes of the sample separation apparatus. Particularly, when such a fluidic valve is configured as a rotary valve, it may be constituted by a stator and a rotor both having fluid conduits. By rotating the rotor relative to the stator, a desired operation mode may be selected. Such a valve may be configured as a shear valve which comprises a first shear valve member as a stator, and a second shear valve member as a rotor. By rotating the second shear valve member, the first and second shear valve members can be moved with respect to each other. The first shear valve member comprises a plurality of ports. A fluid conduit such as a capillary, for instance a glass or metal capillary, can be coupled to each port respectively.

In an embodiment, the fluidic valve is configured to be switchable to a first operation mode in which the fluidic interface fluidically coupled downstream of the first fluid drive is in fluid communication via the fluidic valve with the fluidic interface fluidically coupled to one of the fluid outlet terminals, and in which the fluidic interface fluidically coupled to the second fluid drive is in fluid communication via the fluidic valve with the fluidic interface fluidically coupled to the other one of the fluid outlet terminals. Thus, in the first operation mode, it is always ensured that the two fluid drives are in fluid communication so that a pressure equilibration continuously remains enabled. Hence, a controlled pressure at one interface of the valve will result in an at least approximately controlled pressure at another interface of the valve.

It is also possible that the fluidic valve is configured to be switchable, starting from the first operation mode, to a second operation mode in which the fluidic interface fluidically coupled downstream of the first fluid drive is in fluid communication via the fluidic valve with the fluidic interface fluidically coupled to the other one of the fluid outlet terminals, and in which (at the same time) the fluidic interface fluidically coupled to the second fluid drive is in fluid communication via the fluidic valve with the fluidic interface fluidically coupled to the one of the fluid outlet terminals. Since also in the second operation mode fluid communication between the two fluid drives remains enabled, pressure slopes/ramps, drops or ripples are also suppressed in this state. Only during the extremely short time interval for switching the switching valve between the first and the second operation mode (for instance several milliseconds), the two fluid drives may be fluidically decoupled from one another. However, since this switching time may be as short as 20 ms or even shorter, this will not have a noteworthy impact on the continuous pressure characteristics. Also, by employing a so called 'make-before-break' switching regime this blockage may be further reduced in time or even avoided completely. Important in one embodiment is also the fact, that at no time during operation a pressure in certain segments of the system, particularly in the segment between the separation units, is discharged to a low pressure, particularly to atmospheric pressure, and that no depressurized fluid or system segment gets included into or connected to an already pressurized fluidic segment or sub-segment.

In an embodiment, the first valve member comprises one or more ports forming the fluidic interfaces, and the second valve member comprise one or more grooves for fluidically coupling different fluidic interfaces depending on a switching state of the fluidic valve. Thus, a fluid flow may be enabled between an inlet port, a certain one of the grooves and an outlet port. By rotating the grooves along the arrangement of the ports, different fluid communication and paths can be adjusted, while disabling flow along other paths.

In an embodiment, at least one of the first fluid drive and the second fluid drive may be at least a binary fluid pump. The term "binary fluid pump" may particularly relate to a configuration in which the fluid pump pumps a corresponding mobile phase with a composition of two components. For example, when such a binary solvent composition is used for a chromatography gradient run, the ratio between water as a first solvent and acetonitrile (ACN) as a second solvent may be adjusted so as an individual fraction may get trapped and later released on a chromatography column. However, other pumps such as a ternary or quaternary pump may be used as well. Also a combination of multiple isocratic pumps may be used to form the compositional gradient. In still another embodiment one or both of the fluid drives may be an isocratic pump, i.e. only capable of delivery of constant solvent composition.

In an embodiment, the fluidic valve is switchable so that pressure conditions in the first separation unit and in the second separation unit remain basically constant upon switching and during the entire gradient run. One aspect is, that there is no situation where a loop's content has to be brought to pressure quickly. Another aspect is, that fast $2^{nd}$-dimension gradient does not introduce a pressure respiration. Yet a third aspect is that the pressure conditions inside the $1^{st}$-dimension separation unit will not (or at least to a lesser extent) be modulated by the $2^{nd}$-dimension cycles. This may significantly improve robustness of operation and the performance of the separation, particularly of the chromatographic separation. The arrangement of the fluidic interfaces of the fluidic valve in relation to the fluid drives and the separation units may allow to achieve these conditions. Without pressure slopes/ramps, drops or ripples, artifacts and deteriorating impact on the fluid separating material in the separating units will be diminished, as the stress dynamics is significantly reduced.

In an embodiment, the sample separation apparatus comprises a detector for detecting components of the separated fluidic sample and being arranged in the fluid outlet terminal downstream of the second separation unit. Thus, a detector for detecting the individual fractions and sub-fractions may be arranged downstream of the second separating unit. Such a detector may operate on the basis of an electromagnetic radiation detection principle. For example, an electromagnetic radiation source may be provided which irradiates the sample passing through a flow cell with primary electromagnetic radiation (such as optical light or ultraviolet light). In response to this irradiation with primary electromagnetic radiation, there will be an interaction of this electromagnetic radiation with the fluidic sample so that this interaction can be detected based on variations in properties of the primary radiation (such as intensity, frequency, spectral distribution, propagation direction, vector of polarization or the like) or based on eventually emerging resulting secondary electromagnetic radiation, the said interaction being indicative of the concentration and kind of sample components contained in the fluidic fractions.

In an embodiment, the sample separation apparatus comprises a sample injector for introduction of the fluidic sample into the separation system upstream of the first separation unit. In such a sample injector, an injection needle may intake a metered amount of fluidic sample into a connected loop. After driving and inserting such an injection needle in a corresponding seat and upon switching a fluid injection valve, the fluidic sample may be injected into the path between first fluid drive and first separating unit. Upon such a switching operation, a mobile phase transported by the fluid drive and constituted by a solvent composition transports the sample to the separation unit and may get partially mixed with the fluidic sample.

In an embodiment, the first fluid drive is operable with a first flow rate (pumped fluid volume per time interval) being smaller than a second flow rate (pumped fluid volume per time interval) according to which the second fluid drive is operable. Due to the two-dimensional separation procedure, the amount of solvent per time interval pumped by the first fluid drive may be significantly smaller than another solvent composition pumped by the second fluid drive. This is a natural result in comprehensive 2D-LC simply because the $2^{nd}$-dimension separation basically is sampling the $1^{st}$-dimension fractions. Also a pressure (for instance a pressure value in a range between 50 bar and 400 bar, for instance 200 bar) applied across the first separation unit may be smaller than a pressure (for instance a pressure value in a range between 500 bar and 1500 bar, for instance 800 bar) applied by the second fluid drive across the second separation unit.

In an embodiment, the second flow rate is at least five times, particularly is at least ten times, more particularly is at least fifty times, of the first flow rate. For example, a flow rate of the second fluid drive may be in a range between about 1 ml/min and about 10 ml/min, whereas a flow rate of the first fluid drive may be in a range between about 10 µl/min and about 500 µl/min.

In an embodiment, the sample separation apparatus comprises a control device configured for controlling one or more of the fluidic devices thereof to keep the pressure at the position or in the segment at a predefined value. Hence, the control unit such as a microprocessor or the like may control operation of the first supply unit, a pumping performance of the second supply unit and/or a switching characteristic of the fluidic valve. It may be configured so that the flow rate of the fluid is allowed to vary over time. In accordance to this, the parameter kept constant over the measurement may be the pressure.

In an embodiment, the sample separation apparatus comprises a control device configured for controlling the first separation unit to execute a first separation within a defined measurement volume interval (in accordance with a given first run or gradient volume indicating a volume of a mobile phase needed for separation on the first separation column) for separating the fluidic sample into a plurality of fractions, and controlling the second separation unit to execute a sequence of second separations (each in accordance with a given second run or gradient volume indicating a volume of a mobile phase needed for performing a separation on the second separation column) within the measurement volume interval for further separating at least a part of the separated plurality of fractions into a plurality of sub-fractions. In the context of this application, the term "first separation" may particularly denote a procedure according to which a fluidic sample is to be separated in the first separation unit based on a first volume-based control scheme. This may include a plurality of steps to be carried out subsequently. The execution of these steps occurs over a so-called measurement volume interval. In a preferred embodiment, the first separation is a gradient run by which the fluidic sample is separated in the first separation unit by changing a ratio of two solvents gradually, thereby selectively trapping and later releasing individual fractions of the fluidic sample on the first separation unit. In the context of this application, the term "plurality of second separations" may particularly denote separations which are to be executed by the second separation unit based on a second volume-based control scheme. In a preferred embodiment, each of the second separations is executed over a time interval being smaller than the measurement time interval relating to the first separation. In other words, several or many second separations may be carried out within a time interval of the first separation. This means that the fluidic sample is split, chopped or separated into the various fractions during execution of the first separation, whereas the second separations, further separate the separated fractions into further subfractions by applying another, at least partially different, if not completely orthogonal separation criterion. For instance, a number of second separations relating to one first separation may be in a range between 5 and 1000, particularly between 10 and 200, furthermore, as the volumetric flow rate in the first separation usually is at least ten times lower than the flow rate in the second separation, in terms of retention volumes the factor may range a decade higher. In the context of this application, the term "measurement interval" may particularly denote an entire or a part of a volume interval of a mobile phase required for executing the first separation. Such a volume interval may be in a range between 50 µl and 50 ml, particularly between 400 µl and 4 ml. It may relate to the total volume of the separation unit and to the volume of a mobile phase required for executing a separation run on a first separation unit configured as a liquid chromatography column. In accordance with the long-lasting first separation, the sample can be separated into a plurality of fractions by a first separation criterion (for instance the hydrophobicity, the molecular mass, etc.). In the subsequent, at least partially orthogonal second separations, each fraction separated during the first separation can be further separated into a plurality of sub-fractions (particularly in accordance with another separating criterion such as chemical property of the particles). The result of such a separation can be displayed as a topographic map in a two-dimensional coordinate system (or as a surface in a 3-dimensional coordinate system), both axes representing the corresponding retention volume in a first or a second separation respectively.

In an embodiment, the first separation unit and the second separation unit are configured so as to execute the respective sample separation in accordance with different separation criteria, particularly in accordance with at least partially orthogonal separation criteria. In this context, the term "orthogonal" may particularly denote the low degree or even lack of correlation between the retention parameters in the first and the second dimension in general or at least for the expected sample components. Exemplary embodiments of the invention make benefit of this cognition and propose to adjust the parameters under a consideration of the fact that the separation criteria of the two separation units are not necessarily completely independent from one another.

In an embodiment, the flow coupler comprises at least one check valve preventing fluid from flowing in a reversed direction in at least one of the terminals.

In an embodiment, the first fluid drive and the second fluid drive are both in fluid communication with a flow joiner directly or via a check valve, in at least one, particularly in each, switching state of the fluidic valve. In other embodiments, such a check valve and/or flow joiner may be omitted.

In an embodiment, the system comprises a detector unit arranged downstream of the first separation unit and upstream of the second separation unit. Such a detector unit (for detecting fractions of the fluidic sample) may be arranged in addition to another detector unit being located downstream of the second separation unit.

In an embodiment, the system comprises a sample treatment unit configured for additionally treating the fluidic sample after treatment by the first separation unit and before being delivered into the second separation unit, For instance, such an additional treatment may be an addition of chemical reagents, a chemical modification, a chemical derivatization, a reaction detection, a catalytic transformation, an irradiation, and/or a heating.

In an embodiment, the pressure is adjusted at the predefined position by controlling the flow rate of the second fluid drive. The flow rate may be the transported fluid volume per time interval.

In an embodiment, the pressure is adjusted at the predefined position even when a gradient program of the second fluid drive will change the viscosity of the fluid flowing through the second separation unit.

In an embodiment, the first separation unit and/or the second separation unit may be configured for performing a separation in accordance with liquid chromatography, supercritical-fluid chromatography, capillary electrochromatography, electrophoresis and gas chromatography. However, alternative separating technologies may be applied as well.

The first and/or second separation unit may be filled with a separating material. Such a separating material which may also be denoted as a stationary phase may be any material which allows a different degree of interaction with sample components so as to be capable of separating different components of such a sample. The separating material may be a liquid chromatography column filling material or packing material comprising at least one of the group consisting of polystyrene, zeolite, polyvinylalcohol, polytetrafluoroethylene, glass, polymeric powder, carbon, graphite, alumina, zirconia, silicon dioxide, and silica gel, or any of above with chemically modified (coated, capped, etc.) surface. However, any packing material can be used which has material properties allowing a sample passing through this material to be separated into different components, for instance due to different degrees of interactions or affinities between the packing material and fractions of the analyte. In still another embodiment a sample separation unit, particularly a second sample separation unit, may be a so called open tubular column, i.e. a channel without filling material but with walls capable of selective interaction with sample components.

At least a part of the first and/or second separation unit may be filled with a separating material, wherein the separating material may comprise beads having a size in the range of essentially 0.1 µm to essentially 50 µm. Thus, these beads may be small particles which may be filled inside the separation section of the microfluidic device. The beads may have pores having a size in the range of essentially 0.005 µm to essentially 0.2 µm. The fluidic sample may enter the pores, wherein an interaction may occur between the fluidic sample and the surface of the pores.

The sample separation apparatus may be configured as a fluid separation system for separating components of the sample. When a mobile phase including a fluidic sample is passed through the fluidic device, for instance by applying a high pressure, the interaction between a filling of the column and the fluidic sample may allow for separating different components of the sample, as performed in a liquid chromatography device.

However, the sample separation apparatus may also be configured as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the filling of the column, the different sample components may be distinguished, and one component or band of material may be selectively isolated as a purified sample.

The sample separation unit may be a chromatographic column for separating components of the fluidic sample. Therefore, exemplary embodiments may be particularly implemented in the context of a liquid chromatography apparatus.

The sample separation apparatus may be configured to conduct the mobile phase through the system by means of a high pressure, particularly of at least 400 bar, more particularly of at least 1000 bar.

The sample separation apparatus or its parts or sub-units may be configured as a microfluidic device. The term "microfluidic device" may particularly denote a fluidic device as described herein which allows to convey fluid through microchannels having a dimension in the order of magnitude of less than 500 µm, particularly less than 200 µm, more particularly less than 100 µm or less than 50 µm or less. The sample separation apparatus may also be configured as a nanofluidic device. The term "nanofluidic device" may particularly denote a fluidic device as described herein which allows to convey fluid through nanochannels having even smaller dimensions than the microchannels.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

FIG. 1 illustrates a liquid chromatography system according to an exemplary embodiment.

FIG. 2 illustrates a sample separation apparatus according to an exemplary embodiment and shows schematically different phases of operation corresponding to different valve positions.

FIG. 3 illustrates a first separation according to which the first dimension chromatographic column is operated in accordance with a first volume-based control scheme.

FIG. 4 illustrates another diagram showing a sequence of multiple second separations as performed by a second dimension liquid chromatography column in accordance with a second volume based control scheme.

Figure 5:
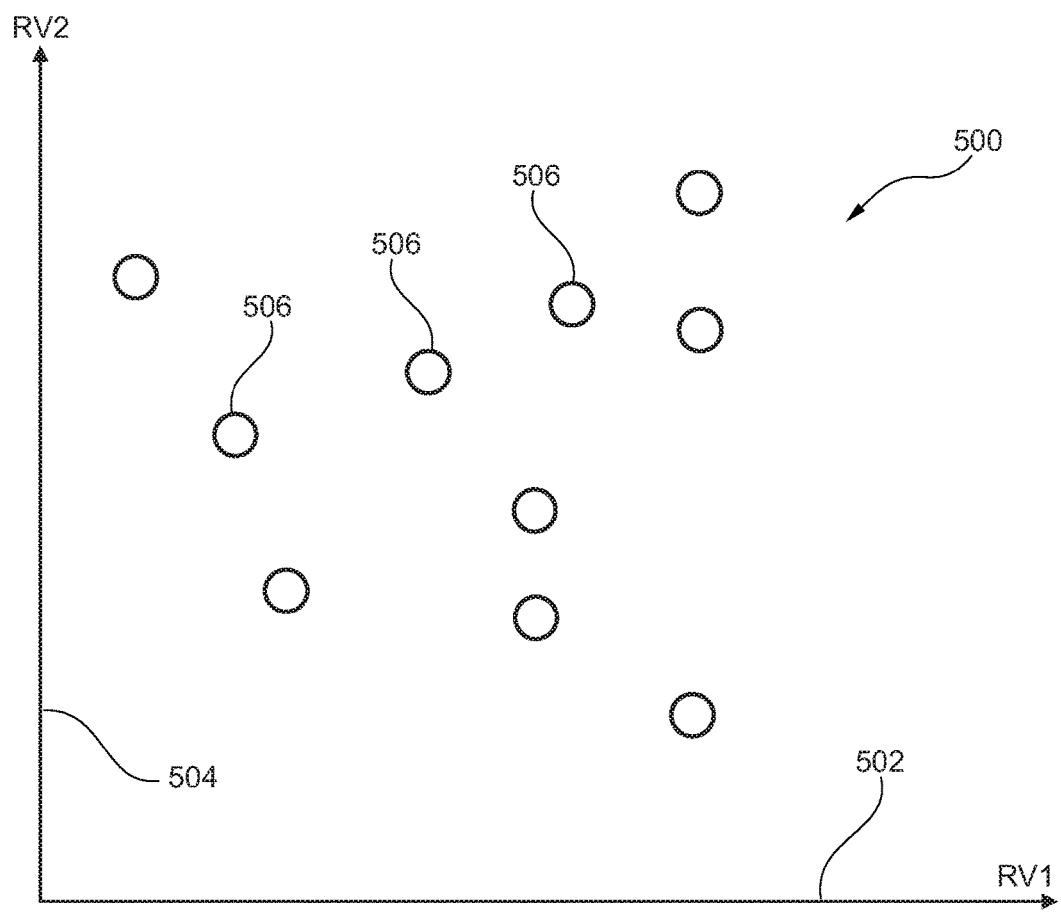
FIG. 5 illustrates a diagram which shows the result of a two-dimensional liquid chromatography experiment, wherein the respective retention volumes are plotted along the two coordinate axes.

The illustrations in the drawings are schematic.

According to an exemplary embodiment of the invention, a two-dimensional liquid chromatography (2D-LC) system with a constant pressure mode is provided for precise and reliable second dimension separations. A special control mode is provided for tandem-LC to support rapid separations (of less than 30 seconds).

In 2D-LC, often there is a requirement to have both a very fast execution of elution gradients, and accurate and precise delivery of flow at a target compositional gradient. The term "UHPLC" is describing systems with even increased requirements in terms of speed and pressure. In an ever increasing interest to increase peak capacity (total number of peaks that can be isolated in a single experiment) several parameters are optimized. This includes smaller size of packing material, smaller separation columns, faster linear speed of solutes during separation, faster compositional gradients, longer separation beds, etc. Putting all this together leads to the fact that proper or optimized operation will happen under high stress in rapid cycles. This may bring together two problems basically: a) predictable performance under dynamic conditions, and b) reliable operation under frequent repeated stress.

In order to achieve speedy and predictable gradients, it is advantageous to avoid excessive dispersion of the fluid flow and excessive elasticity of the system and its elements. Elements like mixers or dampers can be avoided for this purpose. This way the bandwidth of systems may be increased, which then increases demands on the robustness due to stronger impact of dynamic disturbances.

In view of the foregoing, when using tandem-LC configurations, the pressure level on the first dimension column is basically offset by the pressure drop across the second dimension column. Usually, when a gradient is run, for instance in reversed phase separations from water to organic, the viscosity is modulated, which in turn results in a pressure profile (with pressure variation by a factor of three for acetonitrile (ACN) or methanol (MeOH)). Tandem-LC in itself brings key advantages usable by embodiments of the invention:

i) elimination of pressure-breakdown on modulation, which is advantageous for baseline quality and repeatability of separations;

ii) it results in an improved lifetime for the modulator valve, but operation in a constant pressure mode will end up in even superior behavior in these extra aspects;

iii) in view of the reduction of pressure variation on second dimension gradients, the repeated pressure cycles in sub-minute time range can be eliminated, and this results in improved lifetime for the heavily loaded column;

iv) since there is no pressure modulation at the outlet of the first dimension separation unit, there are no more common-mode pressure cycles in sub-minute time range, which results in improved precision and a more predictable separation performance in the first dimension;

v) due to net improvement in speed of the second dimension separation by up to 25%, there is either a shorter repetition time possible resulting in an increased sampling rate, or lower net flow and pressure levels, leading to improved hardware lifetime.

Moreover, there are several additional aspects to be considered for real application of exemplary embodiments of the invention:

A) the gradient execution is volume-based in an embodiment, thus it may not be at a given time slice but rather a volume slice, defining an amount of the fluid to be passed into the second dimension per one second separation; and it may need a control over the first dimension run-volume slice to adjust for this;

B) a corresponding user interface may allow to keep an overview about what is programmed, data analysis, results extraction and quantitative reporting.

The constant pressure mode may be applied in both the first dimension and the second dimension.

Referring now in greater detail to the drawings, FIG. 1 depicts a general schematic of a liquid separation system 10. A first pump 20 receives a mobile phase (also denoted as fluid) as a whole or as individual components that get mixed together by the first pump 20, from a first solvent supply 25, typically via a first degasser 27, which degasses and thus reduces the amount of dissolved gases in the mobile phase. The first pump 20—as a mobile phase drive—drives the mobile phase through a first separating device 30 (such as a chromatographic column) comprising a stationary phase. A sampling unit 40 can be provided between the first pump 20 and the first separating device 30 in order to subject or add (often referred to as sample introduction) a sample fluid (also denoted as fluidic sample) into the mobile phase. The stationary phase of the first separating device 30 is configured for separating compounds of the sample liquid.

A second pump 20' receives another mobile phase (also denoted as fluid) from a second solvent supply 25', typically via a second degasser 27', which degasses and thus reduces the amount of dissolved gases in the other mobile phase. By a fluidic valve 90, the first dimension (reference numerals 20, 30, . . . ) of the two-dimensional liquid chromatography system 10 of FIG. 1 may be fluidically coupled to the second dimension (reference numerals 20', 30', . . . ). The fluidic sample is separated into multiple fractions by the first dimension, and each fraction is further separated into multiple sub-fractions by the second dimension. The way of switching the fluidic valve 90 and a way of arranging the fluidic paths fluidically coupling the two dimensions will be described below referring to FIG. 2.

A detector 50 is provided for detecting separated compounds of the sample fluid. A fractionating unit 60 can be provided for collecting separated compounds of sample fluid.

While each of the mobile phases can be comprised of one solvent only, it may also be mixed from plural solvents. Such mixing might be a low pressure mixing and provided upstream of the pumps 20, 20', so that the respective pump 20, 20' already receives and pumps the mixed solvents as the mobile phase. Alternatively, the pump 20, 20' might be comprised of plural individual pumping units, with plural of the pumping units each receiving and pumping a different solvent or mixture, so that the mixing of the mobile phase (as received by the respective separating device 30, 30') occurs at high pressure and downstream of the pump 20, 20' (or as part thereof). The composition (mixture) of the mobile phase may be kept constant over time, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20, 20' (for instance setting control parameters) and receive therefrom information regarding the actual working conditions (such as output pressure, flow rate, etc.). The data processing unit 70 might also control operation of the solvent supply 25, 25' (for instance setting the solvent/s or solvent mixture to be supplied) and/or the degasser 27, 27' (for instance setting control parameters such as vacuum level) and might receive therefrom information regarding the actual working conditions (such as solvent composition supplied over time, flow rate, vacuum level, etc.). The data processing unit 70 might further control operation of the sampling unit 40 (for instance controlling sample injection or synchronization of sample injection with operating conditions of the pump 20). The respective separating device 30, 30' might also be controlled by the data processing unit 70 (for instance selecting a specific flow path or column, setting operation temperature, etc.), and send in return information (for instance operating conditions) to the data processing unit 70. Accordingly, the detector 50 might be controlled by the data processing unit 70 (for instance with respect to spectral or wavelength settings, setting time constants, start/stop data acquisition), and send information (for instance about the detected sample compounds) to the data processing unit 70. The data processing unit 70 might also control operation of the fractionating unit 60 (for instance in conjunction with data received from the detector 50) and provide data back.

In both sample separation dimensions (first dimension: pump 20, separating device 30; second dimension: pump 20', separating device 30') of the 2D-LC system shown in FIG. 1, operation may be performed in accordance with a volume-based control scheme rather than by a time-based control scheme. Hence, the separation of the fractions and sub-fractions of the fluidic sample is performed in terms of delivered, or run volumes rather than in terms of time slices.

In the following, referring to FIG. 2, a two-dimensional liquid chromatography apparatus 200 according to an exemplary embodiment of the invention will be explained.

The sample separation apparatus 200 is capable of separating a fluidic sample, which is injected by a sample injector 236 into a mobile phase, first into a plurality of fractions (each representing a group of molecules) by a first dimension chromatographic column 204. This separation in a first dimension is performed while the sample is conducted between an inlet 274 and an outlet 270 of the first dimension chromatographic column 204. Later, each of these fractions may be further separated into a plurality of sub-fractions by a second dimension chromatographic column 208. This separation in a second dimension is performed while the sample is conducted between an inlet 272 and an outlet 276 of the second dimension chromatographic column 208. The reason why each of the fractions can further be split into a plurality of sub-sections by the second dimension chromatographic column 208 is that the second dimension chromatographic column 208 may be configured so as to have another separation criterion as compared to the first dimension chromatographic column 204. This may for instance be achieved by different chemicals, different solvent composition, different temperature, used in the two separation systems.

The two-dimensional liquid chromatography apparatus 200 comprises a first binary pump 202. The first binary pump 202 is configured for conducting the fluidic sample to be separated through the first dimension chromatographic column 204. For this purpose, the first binary pump 202 provides a mixture of a first solvent 250 (such as water) and a second solvent 252 (such as acetonitrile, ACN). The first binary pump 202 mixes these two solvents to form a mobile phase composition which is pumped towards the sample injector 236. At the sample injector 236 the actual fluidic sample is added to the mobile phase so the fluidic sample and the mobile phase is then transported towards the first dimension chromatographic column 204. In the sample injector 236, an injection needle can be immersed into a vial accommodating the fluidic sample (not shown). The fluidic sample may then be sucked into the injection needle and a loop fluidically connected thereto. Subsequently, the injection needle may be driven into a seat so as to then introduce the fluidic sample into the mobile phase. In the first dimension chromatographic column 204, the different fractions of the fluidic sample are trapped at the separating material of a column and are later individually released from the column during a gradient run. Therefore, at the fluid outlet of the first dimension separation column 204, the various fractions of the sample are already separated.

Furthermore, a second binary pump 206 is provided which is operated at a significantly higher flow rate as compared to the first binary pump 202. For instance, the flow rate of the second binary pump 206 may be 4 ml/min, whereas a flow rate of the first binary pump 202 may be 100 μl/min. Like the first binary pump 202, also the second binary pump 206 can provide a mixture of a first solvent 254 with a second solvent 256. The solvents 254, 256 may or may not be the same as the solvents 250, 252. The apparatus 200 is configured such that the flow generated by the second binary pump 206 may further transport the fluidic sample, already separated or treated by the first dimension separation column 204 conducted via a fluidic valve 218 towards the second dimension chromatographic column 208 which is arranged downstream of the first dimension chromatographic column 204.

A flow coupler 210 is arranged downstream of the fluidic valve 218. The flow coupler 210 has two fluid inlet terminals 212, 214 and one fluid outlet terminal 216. These "terminals" may also be denoted with the term "conduit" since these parts have protruded volume. As can be taken from FIG. 2, the fluid outlet terminal 216 is fluidically connected to the second dimension chromatographic column 208. Alternatively, the flow coupler 210 may be integrated into the fluidic valve 218 as a part, as a specific section or by function.

The fluidic valve 218 has, in the present embodiment, four fluidic interfaces 222, 224, 226, 228. However, in other embodiments, the number of fluidic interfaces may be different and the valve configuration may be different. A first fluidic interface 222 is connected to the first binary pump 202 via the first dimension separation unit 204. A second fluidic interface 224 is connected to the first fluid inlet terminal 212 of the fluidic coupler or flow coupler 210. A third fluidic interface 226 is connected to the second fluid inlet terminal 214 of the fluidic coupler or flow coupler 210. A fourth fluidic interface 228 is directly coupled with the second binary pump 206.

Furthermore, a control unit 70 (such as a processor, for instance a microprocessor or a central processing unit, CPU) is provided which is capable of controlling all the devices and fluidic components shown in FIG. 2. This is illustrated schematically by the arrow lines directed from the control unit 70 towards the corresponding components.

Inter alia, the control device 70 is also capable of taking control over switching the fluidic valve 218. Particularly, the fluidic valve 218 can be switched by the control device 70 so that the outlet 270 of the first separating unit 204 and the second dimension binary pump 206 remain always in fluid communication with one another, which holds for all switching states of the fluidic valve 218. FIG. 2 illustrates a first switching state 260 and illustrates a second switching state 271. In both operation phases or switching states, certain grooves (not shown) and corresponding ports (not shown) of the two valve members (a rotor and a stator, not shown) are aligned such that the above condition is always fulfilled: The outlet 270 of the first separating unit 204 and the second dimension binary pump 206 remain always in fluid communication with one another, i.e. are hydraulically coupled. This provides the advantageous effect that no or basically no abrupt pressure variations occur as a result of the switching of the fluidic valve 218. In both operation phases 260 and 271, which may be functionally identical or similar the second dimension binary pump 206 is operated in gradient mode at a flow significantly exceeding that generated by the first dimension binary pump 202. Thus the fluid transported or delivered by the second dimension binary pump 206 is only slightly diluted in the flow combiner 210 by the other flow, which is generated by the first dimension binary pump 202. Depending on the switching state 260, 271, a fluidic conduit 290 or 292 in which the larger flow occurs, is changed. In the respective other fluidic conduit 292 or 290, the smaller flow occurs.

Furthermore, a detector 234 is provided which is capable of detecting the separated components of the fluidic sample by an electromagnetic radiation based detection principle. In a particular embodiment, the separated fluidic sample flows through a flow cell 284 and is irradiated with electromagnetic radiation (e.g., a beam 282) from a light source 280. The beam 282 of the light source 280 is passes through the flow cell 284 and can be detected by the detector 234. For instance, an absorbance measurement may be performed. The wavelength range in which a measurement is carried out can for instance be in the visible range or in the ultraviolet range.

After having passed the detector 234, the fluidic sample will be collected in a waste container 286 or collected by a fractionating unit 60. It should be mentioned that in the whole fluidic path the fluidic sample is under a pressure being higher (particularly significantly higher) than ambient pressure at any location upstream of the outlet terminal 276 of the second dimension separation column 208 which is advantageous for pressure ripple suppression.

The control device 70 is capable of executing a certain sequence of procedural steps for performing the actual two-dimensional liquid separation procedure.

By a rapid switching of the modulator valve 218, it chops short portions of the fluidic sample which is already separated by the first dimension column 204 and alternately guides those to the respective conduits 212 and 214 in the corresponding valve switching states. For instance in the switching state 260 the part of the sample deposited in the conduit 214 is guided towards the second dimension column 208 by the flow generated by the second dimension binary pump 206. Simultaneously the conduit 212 is being slowly filled with the fluidic sample already separated by the first dimension column 204. After switching to the state 271 the part of the sample previously deposited in the conduit 212 is guided towards the second dimension column 208 by the flow generated by the second dimension binary pump 206. Simultaneously the conduit 214 is being slowly filled with the fluidic sample already separated by the first dimension column 204. It should be noted, that the fluid displaced at this time from the conduit 214 into the flow joiner 210 represents pure mobile phase provided by the second dimension binary pump 206 during column regeneration after a previously accomplished separation and does not contain sample components as long as the volume of the conduit 214 is not completely displaced. An advantage of this is that due to the modulation valve 218, there are no pressure shocks during switching of the valve 218, since the already separated fluidic sample portion of interest is, at the time of the switching, already at the proper pressure value. Apart from the waste 286 at the very end of the fluidic path, there is no way for the fluid in the fluid conduits of FIG. 2 to escape. Therefore, it is a completely closed fluidic system which is pressure-less only at the very end of the fluidic path (i.e. at the position of the waste 286). Also any possibility of a sample loss prior to second dimension separation is excluded.

The architecture of FIG. 2 is significantly simpler than conventional approaches, since a single valve 218 is sufficient. Particularly, the fluidic coupling of the modulator valve 218 with the fluidic T-piece 210 allows to eliminate abrupt pressure changes or shocks. The pressure which is generated in the second dimension is, via the T-piece 210, always applied at the outlet of the first dimension, so that the second dimension provides a pressure offset for the entire first dimension.

FIG. 2 shows schematically the first operation mode 260 and the second operation mode 271 corresponding to the different positions of the modulator valve 218.

In general terms, the fluidic valve 218 is, in the shown embodiment, not an ON/OFF valve (although it can be formed with a set of simple ON/OFF valves). Seen from its four ports 222, 224, 226, 228, it operates as a cross-over switch.

While in switching state or operation mode 260 (here represented by the dotted lines) the fluidic valve 218 connects the inlets straight to the outlets, and during switching state or operation mode 271 (here the solid lines) the inlets are cross-wise connected to the outlets. In any of these switching states, the T-junction 210 connects the outlet from the first dimension column 204 and the outlet from the second dimension pump 206. The difference is basically, where and at what flow rate the eluted volume from the first dimension column 204 ends up to be traveling (or stored), while the other branch is driven heavily at high flow rates to forward the second dimension gradient onto the second dimension column 208. On the back-swing of the second dimension gradient this other branch is then filled (flushed) with starting composition of the gradient, after which the flipping of the fluidic valve 218 is triggered. After switching now the first dimension result elutes into this other branch, while the previously eluted volume from the initial branch is driven by the second dimension pump 206 towards the second dimension column 208 for final separation. It is true that at the same time this second dimension sample plug is slightly diluted by the starting composition at the given actual first dimension flow rate. Purposely this dilutes not only the second dimension sample, but also the matrix that it is dissolved in. By modulating or tuning first dimension and second dimension flows to an advantageous relation, this may improve stacking of sample on the head of the second dimension column 208, further improving resolution and thus peak capacity of the separation system 200. Furthermore, for each second dimension separation the composition provided by the second dimension pump 206 may be adjusted so as to provide a desired gradient shape or composition at the port 216 based on the knowledge of composition (provided and stored during a swing off of a previous second dimension gradient) and flow rate of the admixed fluid coming out of the branch currently connected to the outlet of the first dimension column 204.

In the shown embodiment, the control unit 70 controls the first pump 202, the second pump 206 as well as the fluidic valve 218. Hence, the control unit 70 coordinates switching of the fluidic valve 218 with the control of the pump operation of pumps 202, 206. Moreover the piston motion of the pump 202, 206 may be synchronized and adapted to correspond to the switching times of the fluidic valve 218.

Advantageously, the control device 70 is configured for, usually indirectly, adjusting the pressure in the segment or fluidic path between the first separating column 204 and the second separating column 208 to a constant value. More precisely, the control device 70 controls or commands the pumps 202, 206 and/or other (sub) units of the system so as to adjust pressure. This can for instance be performed by adjusting the flow rate conveyed by the second pump 206 and optionally also adjusting the flow rate of the first pump 202 in a coordinated manner. By keeping the pressure value between the first separating unit 204 and the second separating unit 208 at a constant level over the entire separation procedure (or alternatively to follow a predefined course, for instance a pressure program over volume, over the entire separation procedure), the fluidic components associated therewith are only subjected to a constant mechanical stress over the entire separation procedure so that their damage or deterioration in view of a pressure variations can be suppressed or even eliminated. Therefore, the lifetime or service intervals of the entire separation system 200 can be significantly increased by controlling the fluidic path between the separating units 204 and 208 to operate under constant (or at least defined) pressure conditions. Thus, a two-dimensional chromatogram (or separation results) can be acquired in dependence of the run volume, i.e. the volume of mobile phase flowing through the respective separating columns 204 and 208 during the liquid chromatography separation, whereas the run volume for the first dimension is preferably registered starting at the start of the first dimension separation, and whereas the registered run volume for the second dimension is preferably reset and registered ab initio with each valve switching, i.e. at the start point of each and every second dimension separation. Thus, particularly applying a volume based liquid chromatographic separation scheme allows the pressure at an outlet of the second pump 206 to be adjusted to a constant value.

For the purpose of pressure regulation, one or more sensors may be implemented particularly along the flow path between the outlet 270 of the first separating column 204 and the inlet 272 of the second separating column 208 to measure an actual pressure value at the respective sensor position. In FIG. 2, some exemplary positions of such a sensor capable of sensing information indicative of a local pressure value at the position of the respective sensor are indicated by crosses. For instance, such a sensor may be located in a fluidic conduit between the outlet 270 of the first separating column 204 and the fluidic interface 222 of the fluidic valve 218, in an internal fluidic conduit of the fluidic valve 218 (i.e. between any pair of fluidically connected fluidic interfaces 222, 224, 226, 228), in a fluidic conduit between one of the fluidic interfaces 224 or 226 and the flow combiner 210, and/or in a fluidic conduit between the flow combiner 210 and the inlet 272 of the second separating column 208. Preferably such a pressure sensor may be located in or be a constituent, component, element or a part of the second dimension pump 206.

The pressure sensor may provide feedback information enabling the control unit 70 to control pressure regulation and adjustment.

Still referring to the operation principle of the control device 70 in the context of a liquid chromatography separation method, FIG. 3 shows a diagram 300 having an abscissa 302 along which a volume (of a conducted mobile phase) delivered by the first pump 202 is plotted and having an ordinate 304 along which a solvent composition as mixed by the first binary pump 202 is plotted. The control device 70 is configured for controlling the first dimension separation column 204 to execute the first separation 306 as shown in FIG. 3 within a measurement volume interval which is denoted with reference numeral 308 in FIG. 3. In the shown embodiment, the measurement volume interval is 30 times a reference volume $V_0$. With this measurement volume 30 $V_0$ of the mobile phase, the gradient run in accordance with the first separation program 306 is carried out.

FIG. 4 shows a diagram 400 indicating a plurality of second separations 402. Diagram 400 corresponds to diagram 300, whereas the volume axis 302 representing the volume delivered by the first pump 202 is shown on another scale. As can be taken from FIG. 4, the control device 70 controls the second dimension separation column 208 to execute all of the plurality of second separations 402 within the measurement volume interval 308. Each of the second separations 402 relates to a volume delivered by the first pump 202 of about the reference volume $V_0$. Thus, in terms of conducted mobile phase volume, many second separations 402 are carried out within one first separation 306. Thus, each of the fractions already separated by the first dimension chromatographic column 204 can be further separated into a plurality of sub-fractions by the second separation column 208. It should be noted, that each one of the plurality of the second separations 402 as shown in the FIG. 4 corresponds to a mobile phase volume of at least $V_0$, delivered by the second pump 206, particularly of at least 2 $V_0$, more particularly of at least 10 $V_0$ or 40 $V_0$. It should also be noted, that the gradient programs for the plurality of the second dimension separations need not necessarily be the same for each second dimension separation but may be changed along with the progress of the first dimension separation.

FIG. 5 now schematically represents a two-dimensional chromatogram 500 as can be obtained when executing the first separation of FIG. 3 and the second separations of FIG. 4. A first retention volume in accordance with the first dimension chromatographic separation (see column 204 and FIG. 3) is plotted along an abscissa 502, whereas a second retention volume in accordance with the second dimension chromatographic separation (see column 208 and FIG. 4) is plotted along an ordinate 504. As can be taken from FIG. 5, a plurality of peaks 506 can be detected.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A sample separation apparatus for separating a liquid sample, the sample separation apparatus comprising:
   a first separation unit configured for separating the liquid sample, the first separation unit comprising an inlet, an outlet, and a first column between the inlet and the outlet, wherein the first column contains a separating material;
   a first pump fluidically coupled to the first separation unit, the first pump configured for generating a first fluid flow for conducting the liquid sample to be separated through the first separation unit, wherein the first pump comprises a movable piston;
   a second separation unit, arranged downstream of the first separation unit, configured for further separating the liquid sample or fractions thereof after separation by the first separation unit, the second separation unit comprising an inlet, an outlet, and a second column between the inlet and the outlet, wherein the second column contains a separating material, and the outlet of the first separation unit is fluidically coupled to the inlet of the second separation unit via a first fluidic path between the outlet of the first separation unit and the inlet of the second separation unit;
a second pump configured for generating a second fluid flow for conducting at least part of the liquid sample after separation by the first separation unit, through the second separation unit, wherein the second pump comprises a movable piston, and the second pump is fluidically coupled to the first fluidic path via a second fluidic path;
a flow coupler comprising at least two fluid inlet terminals in fluid communication with each other and a fluid outlet terminal in fluid communication with the at least two fluid inlet terminals, the fluid outlet terminal being fluidically connectable to the second separation unit;
a fluidic valve comprising a plurality of fluidic interfaces respectively fluidically coupled to the first pump via the first separation unit, to the second pump, and to the inlet of the second separation unit via the at least two fluid inlet terminals, the fluidic valve being switchable to a plurality of switching states for performing the separation of the liquid sample in the second separation unit, wherein the plurality of switching states determine which fluidic interfaces of the plurality of fluidic interfaces are respectively fluidically coupled to the first pump, to the second pump, and to the at least two fluid inlet terminals, and the fluidic valve defines at least a portion of the first fluidic path and a portion of the second fluidic path; and
a control device configured for:
switching the fluidic valve to the plurality of switching states; and
adjusting a pressure at a defined position to a defined value by controlling an operating parameter of at least the second pump, wherein the defined position is in the first fluidic path or the second fluidic path.

2. The sample separation apparatus according to claim 1, wherein the control device is configured for adjusting the pressure at the defined position to maintain the pressure at a constant value.

3. The sample separation apparatus according to claim 1, wherein the control device is configured for adjusting the pressure at the defined position such that the pressure varies according to a defined pressure program.

4. The sample separation apparatus according to claim 1, wherein the control device is configured for controlling at least one of the first pump and the second pump for adjusting a ratio between a flow rate of the second fluid flow generated by the second pump at the defined position and a flow rate of the first fluid flow generated by the first pump to a defined value of the ratio.

5. The sample separation apparatus according to claim 1, wherein the control device is configured for controlling a flow rate of the second fluid flow generated by the second pump for adjusting the pressure at the defined position to the defined value.

6. The sample separation apparatus according to claim 1, comprising a sensor positioned to measure an actual pressure value at the defined position, wherein the control device is configured for receiving sensor data from the sensor indicative of the actual pressure value measured and regulating the pressure at the defined position to the defined value based on the received sensor data.

7. The sample separation apparatus according to claim 1, wherein the defined position is located in a portion of the first fluidic path or the second fluidic path between the fluidic valve and the inlet of the second separation unit.

8. The sample separation apparatus according to claim 1, wherein the defined position is located at or fluidically connected to an outlet of the second pump, or in the second fluidic path.

9. The sample separation apparatus according to claim 1, wherein the control device is configured for adjusting the pressure to the defined value in an entire fluidic path that fluidly communicates with the first separation unit, the second pump and the second separation unit, the entire fluidic path comprising the first fluidic path and the second fluidic path.

10. The sample separation apparatus according to claim 1, wherein the control device is configured for controlling at least one of the first pump and the second pump to execute sample separation by controlling run volumes of fluid flowing through at least one of the first separation unit and the second separation unit.

11. The sample separation apparatus according to claim 1, wherein the control device is configured for separating the liquid sample by modifying a flow rate of at least one of the first fluid flow and the second fluid flow generated by at least one of the first pump and the second pump.

12. The sample separation apparatus according to claim 1, wherein the first pump and the second pump are in fluid communication with one another in at least one of the switching states of the fluidic valve.

13. The sample separation apparatus according to claim 1, wherein the first pump and the second pump are both in fluid communication with the flow coupler in at least one of the switching states of the fluidic valve.

14. The sample separation apparatus according to claim 1, wherein the second separation unit is directly fluidically coupled to the fluid outlet terminal of the flow coupler.

15. The sample separation apparatus according to claim 1, wherein the flow coupler is configured as one of the group consisting of a fluidic T-piece, a fluidic Y-piece, and a fluidic X-piece.

16. The sample separation apparatus according to claim 1, wherein the flow coupler comprises at least one check valve preventing fluid from flowing in a reversed direction away from the second separating unit in at least one of the fluid inlet terminals or the fluid outlet terminal.

17. The sample separation apparatus according to claim 1, wherein the fluidic valve comprises a first valve member and a second valve member being movable relative to one another to thereby adjust a respective switching state of the fluidic valve.

18. The sample separation apparatus according to claim 17, wherein the first valve member comprises a plurality of ports forming the plurality of fluidic interfaces, and the second valve member comprises a plurality of grooves for fluidically coupling different ports of the plurality of ports depending on a selected switching state of the plurality of switching states of the fluidic valve.

19. The sample separation apparatus according to claim 1, wherein the fluidic valve is configured to be switchable to a first state in which the fluidic interface fluidically coupled to the first pump is in fluid communication with the fluidic interface fluidically coupled to a first one of the at least two fluid inlet terminals, and in which the fluidic interface fluidically coupled to the second pump is in fluid communication with the fluidic interface fluidically coupled to a second one of the at least two fluid inlet terminals.

20. The sample separation apparatus according to claim 19, wherein the fluidic valve is configured to be switchable to a second state in which the fluidic interface fluidically coupled to the first pump is in fluid communication with the fluidic interface fluidically coupled to the second one of the at least two fluid inlet terminals, and in which the fluidic interface fluidically coupled to the second pump is in fluid communication with the fluidic interface fluidically coupled to the first one of the at least two fluid inlet terminals.

21. The sample separation apparatus according to claim 1, wherein at least one of the first pump and the second pump is a fluid gradient pump.

22. The sample separation apparatus according to claim 1, comprising a detector positioned to detect the separated liquid sample outputted from the second separation unit.

23. The sample separation apparatus according to claim 1, comprising a sample injector positioned to inject the liquid sample into the first fluid flow generated by the first pump, and being arranged between the first pump and the first separation unit.

24. The sample separation apparatus according to claim 1, wherein the control device is configured to control the first pump such that the first pump generates the first fluid flow at a first flow rate and control the second pump such that the second pump generates the second fluid flow at a second flow rate, and wherein the first flow rate is smaller than the second flow rate.

25. The sample separation apparatus according to claim 24, wherein the second flow rate is selected from the group consisting of: at least five times the first flow rate, at least ten times the first flow rate, and at least fifty times the first flow rate.

26. The sample separation apparatus according to claim 1, wherein the first pump and the second pump are in fluid communication with one another via the flow coupler in each of the plurality of switching states of the fluidic valve.

27. The sample separation apparatus according to claim 23, wherein the control device is configured for controlling the sample injector, the first pump and the second pump to execute a first separation in the first separation unit within a measurement volume interval for separating the liquid sample into a plurality of fractions, and to execute a sequence of second separations in the second separation unit within the measurement volume interval for further separating at least a part of the plurality of separated fractions.

28. The sample separation apparatus according to claim 27, wherein the controller is configured to control at least one of the first pump and the second pump to operate in a gradient mode, in which at least one of the first pump and the second pump generates at least one of the first fluid flow and the second fluid flow as a solvent mixture and varies a composition of the solvent mixture over time.

29. The sample separation apparatus according to claim 27, wherein the controller is configured to control at least one of the first pump and the second pump to operate in an isocratic mode, in which at least one of the first pump and the second pump generates at least one of the first fluid flow and the second fluid flow as a solvent mixture and maintains a constant composition of the solvent mixture over time.

30. The sample separation apparatus according to claim 1, wherein the first separation unit and the second separation unit are configured so as to execute respective sample separations in accordance with different separation criteria.

31. The sample separation apparatus according to claim 1, wherein the first separation unit and the second separation unit are configured so as to execute respective sample separations on identical separation media and with different operating conditions.

32. The sample separation apparatus according to claim 1, comprising a detector unit positioned to detect the separated liquid sample outputted from the first separation unit and being arranged downstream of the first separation unit and upstream of the second separation unit.

33. The sample separation apparatus according to claim 1, comprising a sample treatment unit configured for additionally treating the liquid sample after separation by the first separation unit and before being delivered into the second separation unit.

34. The sample separation apparatus according to claim 1, wherein the first pump is configured for generating the first fluid flow at a pressure of at least 100 bar, and the first separating unit and the second separating unit are liquid chromatography columns.

35. A non-transitory computer readable storage medium comprising instructions stored thereon, that when executed by a computer of or in communication with the sample separation apparatus of claim 1, control the sample separation apparatus to perform a method of separating a liquid sample, the instructions comprising:
  instructions for controlling the first pump to generate the first flow for conducting the liquid sample to be separated through the first separation unit;
  instructions for controlling the second pump to generate the second flow for conducting the at least part of the liquid sample after separation by the first separation unit, through the second separation unit;
  instructions for controlling switching the fluidic valve to the plurality of switching states for performing the separation of the liquid sample in the second separation unit; and
  instructions for controlling adjusting the pressure at the defined position to the defined value.

36. A method of separating a liquid sample, the method comprising:
  conducting the liquid sample through a first separation unit by a first fluid flow generated by a first pump, wherein the first separation unit performs a separation on the liquid sample and outputs the liquid sample in separated fractions;
  conducting at least one fraction of the outputted liquid sample through a second separation unit downstream of the first separation unit assisted by a second fluid flow generated by a second pump,
  wherein a flow coupler comprises at least two fluid inlet terminals in fluid communication with each other and a fluid outlet terminal in fluid communication with the at least two fluid inlet terminals, the fluid outlet terminal being fluidically connectable to the second separation unit;
  switching a fluidic valve to a plurality of switching states for performing sequential separations of the at least one fraction of the liquid sample after separation by the first separation unit, the fluidic valve comprising a plurality of fluidic interfaces respectively fluidically coupled to the first pump via the first separation unit, to the second pump, and to the second separation unit via the at least two fluid inlet terminals, wherein:
    the first separation unit is fluidically coupled to the second separation unit via a first fluidic path between the first separation unit and the second separation unit;
    the second pump is fluidically coupled to the first fluidic path via a second fluidic path;
    the plurality of switching states determine which fluidic interfaces of the plurality of fluidic interfaces are respectively fluidically coupled to the first pump, to the second pump, and to the second separation unit; and the fluidic valve defines at least a portion of the first fluidic path and a portion of the second fluidic path; and adjusting a pressure at a defined position to a defined value, wherein the defined position is in the first fluidic path or the second fluidic path.

37. The method according to claim 36, wherein the pressure is adjusted at the defined position by controlling a flow rate of the second fluid flow.

38. The method according to claim 36, comprising operating the second pump to execute a gradient program that changes a viscosity of the fluid flowing through the second separation unit, wherein the pressure is adjusted at the defined position while the second pump executes the gradient program.

* * * * *